US008067045B2

(12) United States Patent
Smidt et al.

(10) Patent No.: US 8,067,045 B2
(45) Date of Patent: Nov. 29, 2011

(54) NUTRITIONAL FORMULATIONS AND ASSOCIATED METHODS

(75) Inventors: Carsten Smidt, Sandy, UT (US); Mark Bartlett, Provo, UT (US); Jiashi Zhu, San Diego, CA (US); Angela Mastaloudis, Holladay, UT (US)

(73) Assignee: Pharmanex, LLC, Provo, UT (US)

( * ) Notice: Subject to any disclaimer, the term of this patent is extended or adjusted under 35 U.S.C. 154(b) by 87 days.

(21) Appl. No.: 11/444,125

(22) Filed: May 30, 2006

(65) Prior Publication Data

US 2007/0212433 A1 Sep. 13, 2007

Related U.S. Application Data

(63) Continuation-in-part of application No. 11/368,312, filed on Mar. 3, 2006, now abandoned.

(60) Provisional application No. 60/658,337, filed on Mar. 3, 2005.

(51) Int. Cl.
*A61K 36/00* (2006.01)
*C12C 11/00* (2006.01)
*C11B 5/00* (2006.01)

(52) U.S. Cl. .......................... 424/777; 426/14; 426/541

(58) Field of Classification Search .................. None
See application file for complete search history.

(56) References Cited

U.S. PATENT DOCUMENTS

| | | | |
|---|---|---|---|
| 5,942,233 A | 8/1999 | Chang | |
| 6,221,918 B1 * | 4/2001 | Siderov | 514/762 |
| 6,416,806 B1 | 7/2002 | Zhou | |
| 6,629,835 B2 | 10/2003 | Babish et al. | |
| 6,770,585 B2 | 8/2004 | Vuong | |
| 2002/0068098 A1 | 6/2002 | Babish et al. | |
| 2002/0076452 A1 | 6/2002 | Babish et al. | |
| 2002/0077350 A1 | 6/2002 | Babish et al. | |
| 2002/0110604 A1 | 8/2002 | Babish et al. | |
| 2002/0132037 A1 | 9/2002 | Zhou | |
| 2003/0108628 A1 | 6/2003 | Babish et al. | |
| 2003/0158096 A1 | 8/2003 | Craik et al. | |
| 2004/0024275 A1 | 2/2004 | Vuong | |
| 2004/0047926 A1 | 3/2004 | Lam | |
| 2004/0086580 A1 | 5/2004 | Tripp et al. | |
| 2004/0151792 A1 | 8/2004 | Tripp et al. | |
| 2004/0161524 A1 | 8/2004 | Sakai et al. | |
| 2004/0247700 A1 | 12/2004 | Babish et al. | |

FOREIGN PATENT DOCUMENTS

| | | |
|---|---|---|
| EP | 0390040 | 10/1990 |
| GB | 1083815 | 9/1967 |
| JP | 63063622 | 3/1988 |
| WO | WO 01/22934 | 4/2001 |

OTHER PUBLICATIONS http://web.archive.org/web/20030509095459/http://www.whfoods.org/genpage.php?tname=foodspice&dbid=34.*
http://www.aaccnet.org/meetings/2001/Abstracts/a01ma154.htm.*
Li, 2002, Product development of sea buckthorn, Trends in new crops and new uses, pp. 393-398.*
Vuong, A method of preserving and testing the acceptability of gac fruit oil, a good source of beta-carotene and essential fatty acid, 2003, Food Nutr Bull, 24, 372-3.*
Solomon, in response to Vuong and King, "A method of preserving and testing the acceptability og gac fruit oil, a good cource of beta-carotene and essential fatty acids," 2003, Food and Nutrition Bulletin, 24: 372-374.*
Vuong and King, "A method of preserving and testing the acceptability og gac fruit oil, a good cource of beta-carotene and essential fatty acids," 2003, Food and Nutrition Bulletin, 24: 224-230.*
Let Vuong, Stephen R. Dueker, and Suzanne P Murphy, Plasma β-carotene and retinol concentrations of children increase after a 30-d supplementation with the fruit *Mamordica cochinchinensis* (gac). American Society for Clinical Nutrition. 2002. 872-9.
Hiromitsu Aoki, Nguyen Thi Minh Kieu, Noriko Kuze, Kazue Tomisaka and Nguyen Van Chuyen, Carotenoid Pigments in GAC Fruit (*Mamordica cochinchinensis* Spreng), Biosci. Biotechnol. Biochem., 2002, 2479-2482, 66(11).
Doug Burke, Genesis Juice, Feb. 1, 2005.
Pharmanex introduces G3 nutrition drink, scientifically shown to have high levels of antioxidants. Press Release [online], Pharmanex, Mar. 17, 2005 [retrieved on Oct. 11, 2007]. Retrieved from Internet:,URL:http://www.pharmanex.com/corp/pharmanews/pressreleases/03-17-05.shtml.
Clinical study: Validation of non-invasive raman spectroscopy as an indicator of total antioxidant nutritional status in humans. Datasheet [online], Pharmanex. Oct. 2005 (retrieved on Oct. 18, 2007), URL: http://download.oneteamglobal.com/us/info_studies/scanner/ClinicalStudy.pdf.

* cited by examiner

*Primary Examiner* — Patricia Leith
*Assistant Examiner* — Catheryne Chen
(74) *Attorney, Agent, or Firm* — Thorpe North & Western LLP (57) ABSTRACT

Nutritional formulations and methods for imparting positive health benefits to a subject are disclosed and described. In particular, methods and nutritional formulations for providing increased absorption of antioxidants are taught. In some aspects, the nutritional formulation can include Gac fruit extract in combination with at least one other antioxidant. Such nutritional formulations can in some respects produce enhanced or synergistic results with respect to the amount of antioxidants absorbed by a subject.

28 Claims, 4 Drawing Sheets

NUTRITIONAL FORMULATIONS AND ASSOCIATED METHODS

This application is a continuation-in-part of U.S. patent application Ser. No. 11/368,312, filed on Mar. 3, 2006, now abandoned, which claims the benefit of U.S. Provisional Patent Application Ser. No. 60/658,337, filed on Mar. 3, 2005, both of which are incorporated herein by reference.

THE FIELD OF THE INVENTION

This invention relates to formulations and methods for administering a mixture of antioxidants to a subject. Accordingly, the invention involves the fields of botany, nutritional and health sciences, and medicine.

BACKGROUND OF THE INVENTION

In today's modern society, many people are plagued with obesity and poor nutrition. Fast food which is high in calories, cholesterol and salts has become the mainstay for many meals. Most people desire a quick and easy meal regardless of the nutritional value provided. This type of lifestyle is becoming more prolific among many cultures.

Although there is myriad of diseases and disorders which inflict the human body as a result of poor nutrition, two have been on the rise over the recent years, namely heart disease and cancer. The increased risk of developing heart disease and cancer is at least in part attributed to poor nutrition and physical inactivity. It has been suggested that oxidation by free radicals, of the low-density lipoprotein cholesterol (LDL) molecule, plays a central role in the formation and progression of heart disease. Oxidation reactions alter and damage DNA found in healthy cells. Today's stressful lifestyles combined with a lack of physical activity and poor nourishment is a likely cause of increased in-vivo production of free radicals, which in turn can result in an increased risk of heart disease and cancer.

One known mechanism for combating free-radicals is administration of antioxidant compounds. Antioxidant compounds operate by inhibiting oxidant formation, reducing oxidation reactions once they have started, and repairing oxidant-damaged cells. Antioxidants are free radical scavengers, meaning the anti-oxidant compounds safely interact with free radicals to terminate or reduce the oxidation reaction. Many antioxidant compounds are found in natural foods. Examples of antioxidants include are phytochemicals (carotenoids and polyphenols), vitamins (vitamin E and C) including tocopherols, ascorbic acids, and minerals. Some examples of specific antioxidants include vitamins E, C, and A, including beta-carotene, selenium, and flavonoids.

Phytochemical compounds are antioxidants which are mainly found in fruits and vegetables. In particular, carotenoids, such as beta-carotene, are found in many fruits and vegetables such as carrots, spinach, and sweet potatoes. One food which is extremely high in carotenoids is the fruit from *Momodica cochinchinensis Spreng*, also known as Gac fruit.

While antioxidants are known for combating free-radicals, certain antioxidants have higher potencies than others. Furthermore, different antioxidants may have different mechanisms of action by which they address free-radicals, and some antioxidants may be more potent against certain free-radicals than others. Some of the most potent antioxidants are carotenoids and flavonoids. Additionally, lycopene and beta-carotene are considered some of the most efficient singlet oxygen quenching antioxidants. It is believed that lycopene, in particular, may contribute to the prevention of cancer and heart disease.

In view of the forgoing, nutritional formulations and methods which impart positive health benefits and have a broad spectrum of free-radicals protection continues to be sought.

SUMMARY OF THE INVENTION

Accordingly, the present invention provides nutritional formulations and methods for imparting positive health benefits to a subject. In one aspect of the present invention, a method of improving absorption of an antioxidant administered to a subject is provided. The method includes co-administering at least one antioxidant with an effective amount of a Gac Fruit extract.

In another embodiment, an oral dosage composition for delivering antioxidants to a subject is provided. The oral dosage form includes at least one antioxidant and an antioxidant absorption enhancing amount of a Gac Fruit extract.

In yet another aspect of the present invention, a potent antioxidant nutritional formulation is provided. The potent antioxidant nutritional formulation includes a Gac fruit extract present in an amount of from about 3.0 wt % to about 15 wt % of the antioxidant nutritional formulation; a Cili fruit extract present in an amount of from about 0.5 wt % to about 10 wt % of the antioxidant nutritional formulation; a Siberian pineapple extract present in an amount of from about 0.1 wt % to about 20 wt % of the antioxidant nutritional formulation; and a Wolfberry extract present in an amount of from about 0.01 wt % to about 10.0 wt % of the antioxidant nutritional formulation.

DETAILED DESCRIPTION

Figure 1:
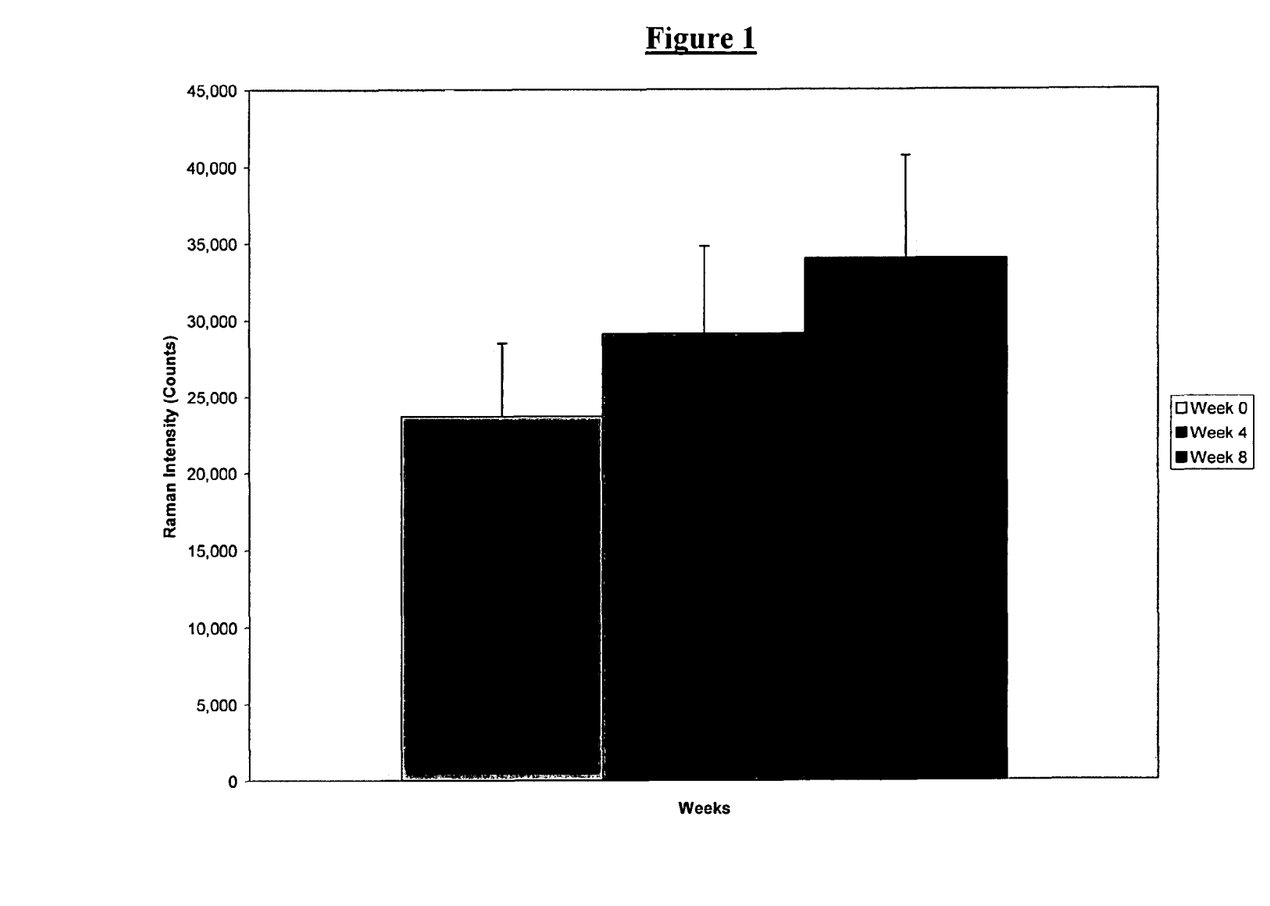
FIG. 1—Is a graphical representation of the Raman Intensity counts at the 0, 4, and 8 week time points of the study group which were administered the Gac Fruit containing nutritional supplement.
Figure 2:
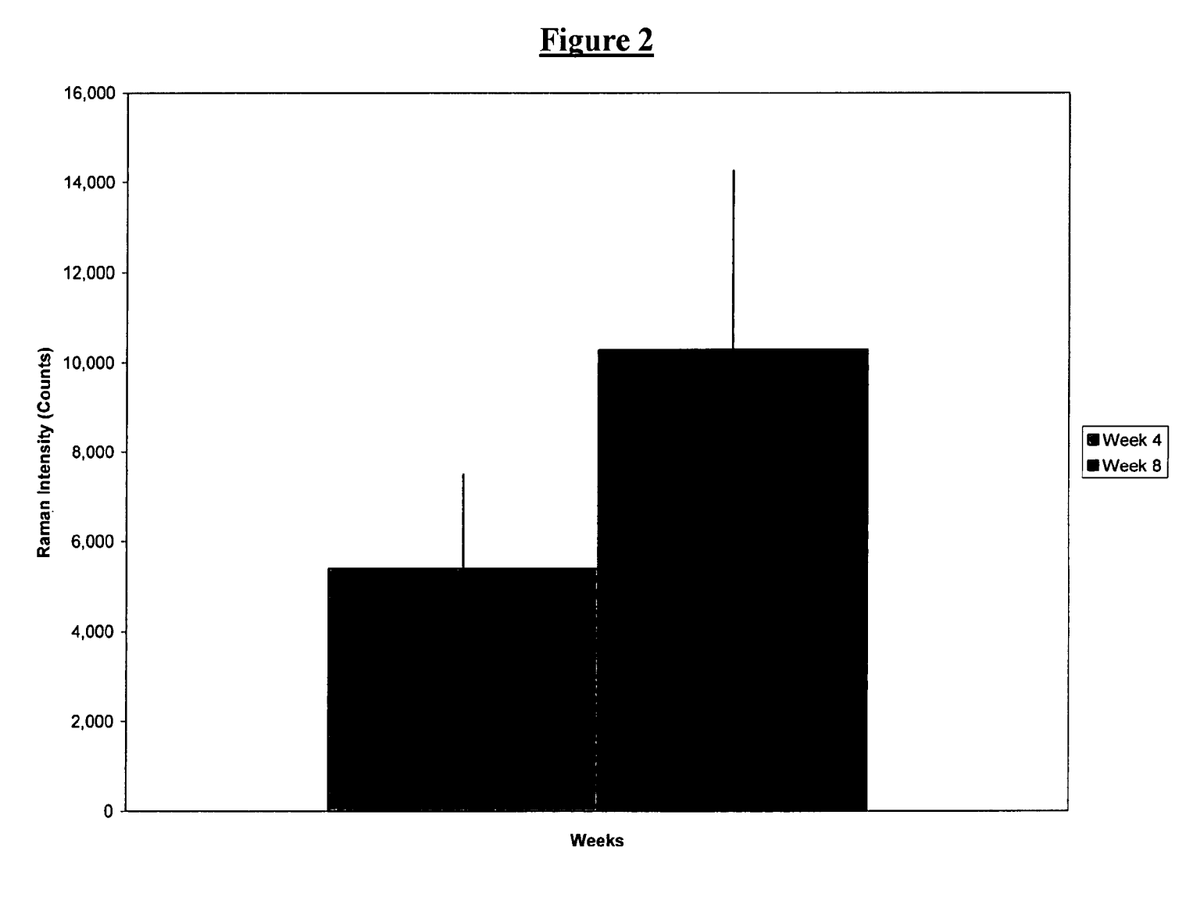
FIG. 2—Is a graphical representation of the change in Raman Intensity counts which occurred at the 4 and 8 week time points of the study group which were administered the Gac Fruit containing nutritional supplement.
Figure 3:
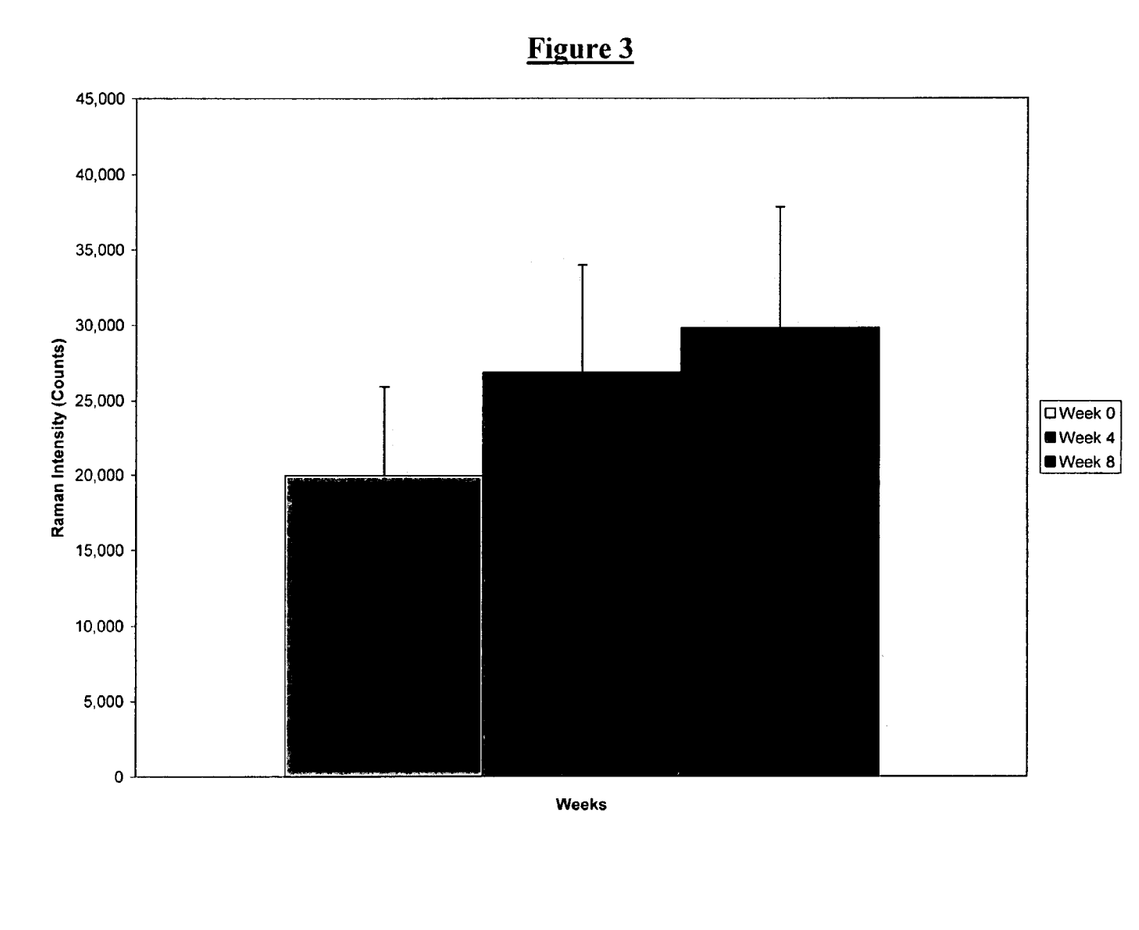
FIG. 3—Is a graphical representation of the Raman Intensity counts at the 0, 4, and 8 week time points of the study group which were administered the conventional antioxidant nutritional supplement formulation.
Figure 4:
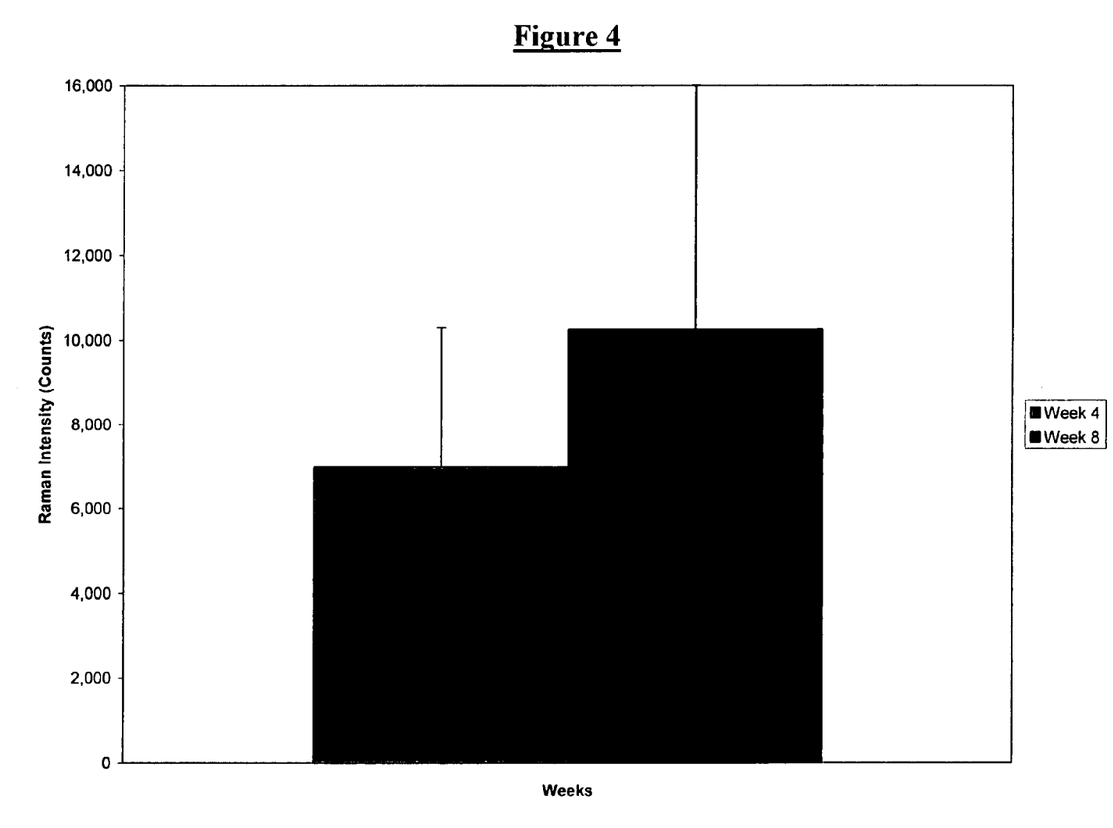
FIG. 4—Is a graphical representation of the change in Raman Intensity counts which occurred at the 4 and 8 week time points of the study group which were administered the conventional antioxidant nutritional supplement formulation.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

Definitions

In describing and claiming the present invention, the following terminology will be used.

The singular forms "a," "an," and "the" include plural referents unless the context clearly dictates otherwise. Thus, for example, reference to "a carrier" includes reference to one or more of such carriers, and reference to "an excipient" includes reference to one or more of such excipients.

As used herein, "formulation" and "composition" may be used interchangeably herein, and refer to a combination of two or more elements, or substances. In some embodiments a composition may include an active agent and a carrier.

As used herein, "effective amount" or "antioxidant absorption enhancing amount" refers to an amount of an ingredient, namely composition, is sufficient to achieve an intended compositional or physiological effect. Thus, a "therapeutically effective amount" refers to a non-toxic, but sufficient amount of an agent, including active agents, to achieve therapeutic results in preventing or ameliorating a condition for which the active agent is known to be effective, or in attaining a desired physiologic effect. It is understood that various biological factors may affect the ability of a substance to perform its intended task. Therefore, an "effective amount," "antioxidant absorption enhancing amount," or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, "carrier" or "inert carrier" refers to a substance with which a bioactive agent or a nutritional agent may be combined to achieve a specific dosage formulation for delivery to a subject. As a general principle, carriers must not react with the bioactive agent in a manner which substantially degrades or otherwise adversely affects the bioactive agent or its potency.

As used herein, "excipient" refers to substantially inert substance which may be combined with an active agent and a carrier to achieve a specific dosage formulation for delivery to a subject, or to provide a dosage form with specific performance properties. For example, excipients may include but are not limited to binders, lubricants, etc., but specifically exclude active agents and carriers.

As used herein, "subject" refers to a mammal that may benefit from the administration of a composition or method as recited herein. Most often, the subject will be a human.

As used herein, "administration," and "administering" refer to the manner in which an active agent, or composition containing such, is presented to a subject. Administration can be accomplished by various routes well-known in the art including oral and non-oral methods.

As used herein, "coadministration" refers to administration of two or more active agents in a manner that will allow them to be present together in-vivo for period of time. Accordingly, while the term "coadministration" includes simultaneous administration of two or more active agents, and administration from a single formulation, it is to be understood that it is not limited thereto.

"Oral administration" can be achieved by swallowing, chewing, or sucking of an oral dosage form comprising the drug. Examples of well known oral dosage forms include tablets, capsules, caplets, powders, granulates, beverages, syrups, elixirs, confections, or other food items, etc.

As used herein, "extract" when used in connection with a plant, tree, herb, fungus, etc., refers to material which has been removed from the source, or a portion thereof, including the flower, fruit, seed, peel, leaf, root, bark, stem, etc. As will be recognized by those of ordinary skill in the art, extracts may be either crude or refined to a selected degree in order to isolate specified materials or active agents. Extracts can take a variety of forms including powders, juices, purees, etc. A number of extraction processes that can be employed to produce the compositions of various types will be recognized by those skilled in the art, such as dehydration, lyophilization, etc.

"Synergistic", "synergism", "synergistically effective" or "synergistically enhances", may be used interchangeably and refer to a situation in which the combined effect of two agents is greater than which would be predicted from their individual effects. Various mechanisms for calculating or otherwise determining synergism are known to those of ordinary skill in the art.

"Antioxidant" refers to a chemical compound, an enzyme or other organic molecule which prevents free radicals from causing oxidation of molecules in the body. Susceptible molecules include without limitation, such vital entities as DNA, RNA, lipids (fats), and proteins. The antioxidant, by reacting with the oxidant, protects these important molecules from being damaged. Examples of antioxidants include without limitation, vitamins A, C, E, carotenoids, polyphenols, and certain minerals.

The term "Gac Fruit," "Gac Extract," "Gac fruit extract," "Gac plant," and "Gac Fruit Puree" refer to a product made from the fruit of all strains and hybrids of the plant *Momordica cochinchinensis Spreng*, or of plants significantly related thereto, grown anywhere in the world including blends, mixtures, and combinations of such strains and relatives.

As used herein, the term "conventional nutritional supplement" refers to antioxidant supplements in any form which do not contain Gac fruit or a Gac fruit extract.

As used herein, the terms "bioavailable" or "bioavailability" when used in connection with antioxidants refer to the antioxidant portion of a nutritional formulation which is absorbed or taken up into a subject's general circulation. The term "enhanced bioavailability" refers to an increase in the percentage of administered antioxidant which is absorbed by the subject into general circulation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 400 should be interpreted to include not only the explicitly recited concentration limits of 0.5 and 400, but also to include individual concentrations within that range, such as 0.5, 0.7, 1.0, 5.2, 8.4, 11.6, 14.2, 100, 200, 300, and sub-ranges such as 0.5-2.5, 4.8-7.2, 6-14.9, 55, 85, 100-200, 117, 175, 200-300, 225, 250, breadth of the range or the characteristic being described.

The Invention

The present invention encompasses methods and nutritional formulations for imparting positive health and nutritional benefits to a subject. In one aspect, such a nutritional formulation includes the extract from Gac fruit in combination with at least one other antioxidant source. In another aspect, a method for antioxidant levels in a subject can include administering the nutritional formulation which includes the extract from Gac fruit in combination with at least one other antioxidant source to the subject. In another aspect of the present invention a nutritional formulation is provided, wherein the active ingredients, such as Gac extract are encapsulated nanoparticles that have been encapsulated by cyclodextrin compounds.

As noted above, antioxidants are one of the many protective compounds found in the body and plants. The main function of antioxidants is to neutralize free radicals in the body. It has been suggested that free radicals cause premature aging, heart disease and cancer. Free radicals are highly reactive byproducts of chemical processes in the body. Free radicals produce harmful oxidation reactions which damage the integrity of cells and body tissues. For these reasons herbal supplements containing antioxidants have become popular in recent years.

It has now been recognized that antioxidants promote strong and healthy immune system, aid in the development of white blood cells, help maintain cell membrane integrity and reduce plaque formation which promote heart disease. Further, antioxidants have special properties that neutralize free radicals. In many cases, a distinctive pattern of alternating single and double bonds found in the antioxidant compounds provides the functionality allowing the compound to absorb excess energy from free radical compounds. Certain antioxidant compounds have higher potencies and have slightly different functions. For example, carotenoids and flavonoids appear to be some of the most potent antioxidants. In addition, different plants supply higher concentrations and potencies of antioxidant compounds.

As will be recognized by those of ordinary skill in the art, antioxidants sources are abundant in nature and can be derived or extracted from many different species of plants. Specific examples of antioxidant compounds that can be utilized in the present invention include without limitation, carotenoids, polyphenols, and tocopherols. In one embodiment the antioxidant compound selected can be beta-carotene. In another aspect of the present invention the antioxidant compound can be lycopene.

The nutritional formulation of the present invention can provide for increases of antioxidant levels in a subject after a period of consumption by the subject. In one embodiment a subjects antioxidant levels can increase by at least about 15% after a period of about four weeks during which the nutritional formulation is consumed twice daily in amounts of about 3 ounces. In another embodiment a subject can experience antioxidant level increases of greater than about 40% after a period of about 8 weeks during which the nutritional formulation is consumed twice daily in amounts of about 3 ounces.

The nutritional formulation of the present invention can provide for increased absorption of antioxidants as compared to an equivalent total antioxidant dosage that does not include Gac Fruit. In one embodiment, the antioxidant absorption is increased by at least about 15% as compared to an equivalent total antioxidant dosage that does not include Gac Fruit. In another embodiment the antioxidant absorption can be increased by at least about 25% as compared to an equivalent total antioxidant dosage that does not include Gac Fruit. In yet another embodiment the antioxidant absorption can be increased by at least about 40% as compared to an equivalent total antioxidant dosage that does not include Gac Fruit.

The nutritional formulations of the present invention can be present in a single nutritional composition or in a combination of multiple formulated nutritional compositions which are co-administered to a subject. In one embodiment, the nutritional formulation is a single liquid nutritional formulation containing an effective amount of Gac extract and at least one antioxidant source.

The nutritional formulations include can include Gac fruit extracts and at least one other antioxidant source. The at least one other antioxidant source can include at least one plant extract. The at least one plant extract can include, but is not limited to Cili fruit (Rosa roxburghii) extracts (which generally exclude the seeds), Wolfberry fruit extracts (Lycium barbarum L. or Lycium Chinese), Sea Buckthorn fruit extracts (Hippophae rhamnoides), and mixtures thereof. Other antioxidants well known in the art may also be included. The at least one plant extract can comprise from about 0.1 wt % to about 25 wt % of the nutritional composition.

In one embodiment, the at least one plant extract can include or consist of a Cili fruit extract and a Siberian pineapple extract. In another embodiment, the at least one plant extract can include or consist of a Cili fruit extract and a Wolfberry extract. In yet another embodiment, the at least one plant extract can include or consist of a Siberian pineapple extract and a Wolfberry extract. In still another embodiment, the at least one plant extract can include or consist of a Cili fruit extract, a Siberian pineapple extract, and a Wolfberry extract.

The Gac component of the present formulation is generally included as a liquefied pulp fraction or extract, and may be obtained by any process of processing, separation or active ingredient extraction known to those skilled in the art. By way of example, without limitation, extraction techniques, such as infusion, tincture, liquid extractions, etc. followed by removal of the liquid portion and concentration of the extract may be used. In other cases, the extract may be a raw extract, and in yet other aspects, solid extracts such as Gac pulp may also used. One method for extracting Gac oil is described in U.S. Pat. No. 6,770,585 which is incorporated herein by reference.

In accordance with the present invention, the amount of Gac extract contained in the nutritional formulation may be varied according the knowledge of one skilled in the art in order to achieve a particularly desired result. However, the Gac extract content may be from about 0.1% wt % to about 20 wt % of the formulation. In one aspect, the amount may be from about 3.0 wt % to about 15 wt % of the formulation. In another aspect, the amount may be from about 4.0 wt % to about 9.0 wt % of the formulation.

Cili fruit extract, when incorporated in the nutritional formulation, can also enhance the health imparting benefits of the formulation. Cili extract is derived from the cili plant which is also indigenous to southwest China. Ciii fruit also sometimes called Rosa Roxburghii & Rosehip. Many ameliorating health benefits are attributed to the consumption of cili extract such as stress, aging, cancer, immunity and atherosclerosis. Cili juice can also increase SOD content in a subject's red blood cells. A biphenol component of Cili is also found in virgin olive oil. It has been suggested that Cili has antioxidant and free radical scavenger capabilities. The Cili juice is rich in vitamin C and E, polyphenols and polysaccharides.

According to one aspect of the present invention, the amount of Cili fruit extract contained in the nutritional formulation may be varied depending on the amount of other extracts present and the desired result. When cili extract is included in the nutritional formulation it can comprise from about 0.5 wt % to about 10 wt % of the nutritional composition. In yet another aspect, the amount may be about 1.0 wt % to about 5.0 wt % of the nutritional composition.

Sea Buckthorn is also known as *Hippophae rhamnoides* or Siberian pineapple, and has been shown to be a source of many vitamins, including vitamin A, E, C, B1, B2, and K. It has also been reported that Sea Buckthorn is a significant source of various fatty acids, such as linoleic, alpha linoleic, oleic, palmitic, and palmitoleic acids. Mainly, Sea Buckthorn is another source for antioxidant compounds such as, carotenoids, tocopherols, flavonoids, fatty acids, sterols and phytosterols. Sea Buckthorn has been used to in the treatment of many diseases and disorders such as, obesity, skin conditions, prevention and treatment of cancer.

The amount of Sea Buckthorn extract contained in the nutritional formulation may be varied depending on the amount of other extracts present and the desired result. When Sea Buckthorn extract is present in the nutritional formulations of the present invention it can comprise from about 0.1 wt % to about 20.0 wt % of the formulation. In one aspect, the amount may be from about 0.5 wt % to about 10 wt % of the formulation.

In another aspect, the amount may be about 4.0 wt % to about 9.0 wt % of the formulation. 5 Wolfberry extract, comes from the Wolfberry plant, also known as lycium or goji berries, which is indigenous to Asia. The Chinese have been utilizing and reaping the benefits of Wolfberry extract for many years. Wolfberries, also known as Chinese Lycium or Goji Berry, provide a rich source of beta-carotene, zeaxanthin, polysaccharides, and vitamins such as vitamin C, E, B1, B2 and B6. Wolfberries have been shown to potentially have immune stimulating action. The naturally occurring antioxidants found in wolfberries have been shown to scavenge free radicals and in return improve the regeneration effects of the body's immune system. In addition it has been suggested that the affects of wolfberries increase the levels of important bodily antioxidant enzymes such as superoxide dismutase (SOD) and glutathione peroxidase (GSHPx) and as a result reduce the affects of aging on the skin, increases vision and protection against cancer.

The amount of Wolfberry extract contained in the nutritional formulation can vary according to the desired antioxidant level and the amount of Gac extract present in the formulation. When present in the nutritional formulations, the Wolfberry extract content will generally be from about 0.01 wt % to about 10 wt % of the formulation. In one aspect, the amount may be from about 0.1 wt % to about 5 wt % of the formulation. In another aspect, the amount may be about 0.2 wt % to about 1 wt % of the formulation The nutritional formulations of the present invention can also include other fruit and/or vegetable juices. The juices may be from concentrate and can be present for a variety of purposes including as flavorants, colorants, or to add bulk to the formulation. Examples additional juices which can be included in the nutritional formulations include but are not limited to pear juice, apple juice, grape juice, tomato juice, carrot juice, cranberry juice, blueberry juice, and combinations thereof. When present in the nutritional formulations, the juice(s) can comprise from about 4 wt % to about 35 wt % of the nutritional formulation.

In addition to the fruit extracts and juices described above, other herbal and botanical extracts may be incorporated into the nutritional formula, which impart positive health benefits. Generally, herbal and botanical extracts are made from all kinds of herb and botanic sources and formulated based on their therapeutic function. For example, anti-flu, bone/joint, brain function, cardiovascular, circulatory, diet, depression, digestion, energy, eye vision, general health, immune system, liver, men's health respiratory, rest, urinary tract, women's health, etc. In one aspect, herbal and botanical extracts for inclusion in the present formulation can be selected from, but not limited to, Ginseng, Ginko Biloba, Dong Quai, Hawthorn berry, St. John's Wort, Saw Palmetto, Kava Kava, Rose Hips, Echinacea, Licorice Root, Grape seed, Chammomile, Hempseed, Aloe Vera, Cinnamon Bark, Cordyceps, Ho Shou Wu, Dandelion, Gynostemma, mushroom, Notginseng, Dan Shen, Noni, Garlic, Nopal, Valerian, Milk Thistle and mixtures thereof may be included.

In one aspect, vitamins either water soluble or oil soluble may be added. Water soluble vitamins specifically contemplated by the present invention include, but are not limited to: vitamin B1, B2, B3, B5, B6, B12, biotin, choline, folic acid, inositol, para-aminobenzoic acid (PABA) but are not limited to: vitamin A, vitamin D, vitamin E, and vitamin K.

Other health imparting substances which may be combined with the desired Gac extract in the formulation of the present invention include amino acids, ionic minerals, and naturally occurring anti-oxidants. The amino acids contemplated include: alanine, arginine, carnitine, gamma-aminobutyric acid (GABA), glutamine, glycine, histidine, lysine, methionine, N-acetyl cysteine, ornithine, phenylalanine, taurine, tyrosine, and valine, but are not limited thereto. Additionally, the ionic minerals contemplated by the present invention for inclusion in an embodiment of the formulation include both anions and cations.

Excipients may also be present in the nutritional formulations of the present invention. Excipients can include stabilizers, preservatives, flavoring agents, thickeners, etc. Non-limiting examples of excipients include xanthan gum, sodium benzoate, natural and artificial flavorings, pectin, and the like. The excipients can be present individually or in combinations. It is important that the excipients do not alter or inhibit the antioxidant potency of the nutritional formulations.

The nutritional formulations of the present invention can also include an amount of water. Water can comprise from about 1.0 wt % to about 95 wt % of the nutritional formulation.

The amount of carotenoid compounds obtained from the fruit extracts may vary from fruit to fruit. Typically, the carotenoid family is responsible for most of the pigments found in plants. For example, carotenoids produce the orange pigments found in pumpkins and carrots, and red pigments in tomatoes. In addition to the color imparting properties, carotenoids as a whole are highly effective at quenching singlet oxygen (an unstable and highly reactive oxygen compound) and are a direct scavenger of free radicals. Carotenoids are defined by their chemical structure. The majority of carotenoids are derived from a 40-carbon polyene chain. The distinctive pattern of alternating single and double bonds in the polyene chain provides the functionality allowing carotenoids to absorb (quench) excess energy from singlet oxygen compounds. Some specific examples of carotenoids are alpha-carotene, beta-carotene, lycopene, astaxanthin, lutein, and zeaxanthin. Lycopene and beta-carotene may be the most effective of the carotenoids at quenching singlet oxygen.

Other antioxidants may have singlet oxygen quenching potential such as, alpha-tocopherol, alpha lipoic acid, flavonoids, etc. Singlet oxygen quencher compounds should have electron-rich structures such as double bonds in the molecules to react with and stabilize singlet oxygen reactions. Flavonoids for example, have been suggested to act as scavengers of various oxidizing species. Flavonoids stem from polyphenol compounds. Generally phenolic compounds, and in most flavanoids and flavonoids, contain groups capable of quenching radicals. The phenolic group is responsible for stabilizing and quenching the unstabilized energy of a free-radical. A high percentage of flavonoids are found mainly in citrus plants, grapes and berries.

In another aspect, the present invention relates to a method of providing a nutritional formulation comprising the active ingredients of an extract from Gac fruit in combination with at least one other antioxidant source. The formulation of the present invention provides for enhanced bioavailability of the antioxidants in the formulation as compared to an antioxidant formulation containing no Gac Fruit or Gac fruit extract.

In yet another aspect of the present invention, a nutritional formulation providing even further enhancement of antioxidant bioavailability is provided. The formation provides a Gac extract, at least one other antioxidant, and at least one cyclodextrin compound. Cyclodextrins are complex compounds once referred to as a sugar, which are macrocyclic hosts that are formed by the action of certain bacterial enzymes on starch. There are three commercially available cyclodextrins, alpha, beta and gamma-cyclodextrin. The inclusion of a cyclodextrin to a formulation may alter different properties of the formulation such as, volatility, solubility and chemical stability. Inclusion of a cyclodextrin compound in the present invention can provide a balanced antioxidant effect in a subject. In particular, the gamma-cyclodextrin compound when incorporated in the present formulation can encapsulate certain carotenoid compounds for increased solubility activity and as a result increase the body's ability to metabolize and absorb the carotenoid compound. Accordingly, in some aspects, the gamma-cyclodextrin compound may be in a 1:1 molar ratio with all carotenoids present in the formulation. In another embodiment the molar ratio can be adjusted to compensate for the fats present in the formulation. It will be appreciated by one skilled in the art that the cyclodextrin compound may encapsulate a variety of compounds, both active and inactive, that are present in the nutritional formulation.

Generally, the nutritional formulation may be provided as a liquid oral dosage form. However, in one aspect of the present invention the nutritional formulation may be a variety of oral dosage forms are well known to those of ordinary skill in the art, and specific formulation ingredients may be selected in order to provide a specific result. Typically, the nutritional formulation is formulated in a beverage oral form. Other oral dosage forms may also be implemented with the present formulation. For example, and without limitation, oral dosage forms such as beverages, powders, tablets, capsules, gel capsules, liquids, syrups, elixirs, and suspensions. Accordingly, in one aspect of the present invention, the composition may be a dosage form selected from the group consisting of beverages, effervescent beverages, liquids, syrups, elixirs, suspensions, tablets, powders, capsules, gel capsules, confections, candies, bars, lozenges, and combinations thereof. In a further aspect of the present invention the beverage dosage form may utilize a powder form of the composition of the present invention, where the beverage formulation utilizes other ingredients, such as sweeteners, colorants and effervescent causing ingredients.

EXAMPLES

The following examples will enable those skilled in the art to more clearly understand how to practice the present invention. It is to be understood that while the invention has been described in conjunction with the preferred specific embodiments thereof, that which follows is intended to illustrate and not limit the scope of the invention. Other aspects of the invention will be apparent to those skilled in the art to which the invention pertains.

Example I

| Formulation | Composition (wt %) |
|---|---|
| Gac Fruit extract* | 3-10 |
| Cili Fruit | 0.5-10 |
| Wolfberry | 0.1-5 |
| Sea Buckthorn | 3-10 |
| Water | 1-95 |
| Excipients** | 0.1-10 |

*Extract should be from Gac Fruit aril (seed membrane). High in carotenoids, lycopene and beta-carotene.
**Excipients can be flavor agents, stabilizers and preservatives.

Example II

| Formulation | Composition (wt %) |
|---|---|
| Gac Fruit extract | 3-10 |
| Cili Fruit | 0.5-10 |
| Wolfberry | 0.1-5 |
| Water | 1-95 |
| Excipients | 0.1-10 |

Example III

| Formulation | Composition (wt %) |
|---|---|
| Gac Fruit extract | 3-10 |
| Wolfberry | 0.1-5 |
| Water | 1-95 |
| Excipients | 0.1-10 |

Example IV

| Formulation | Composition (wt %) |
|---|---|
| Gac Fruit extract | 3-10 |
| Cili Fruit | 0.5-10 |
| Sea Buckthorn | 3-10 |
| Water | 1-95 |
| Excipients | 0.1-10 |

Example V

| Formulation | Composition (wt %) |
|---|---|
| Gac Fruit extract | 3-10 |
| Cili Fruit | 0.5-10 |

-continued

| Formulation | Composition (wt %) |
|---|---|
| Water | 1-95 |
| Excipients | 0.1-10 |

Example VI

| Formulation | Composition (wt %) |
|---|---|
| Gac Fruit extract | 3-10 |
| Sea Buckthorn | 3-10 |
| Water | 1-95 |
| Excipients | 0.1-10 |

Example VII

| Formulation | Composition (wt %) |
|---|---|
| Gac Fruit extract | 3-10 |
| Wolfberry | 0.1-5 |
| Sea Buckthorn | 3-10 |
| Water | 1-95 |
| Excipients | 0.1-10 |

Example VIII

| Formulation | Composition (wt %) |
|---|---|
| Gac Fruit extract | 3-10 |
| Fruit extract* | 5-9 |
| Cili Fruit | 0.5-10 |
| Wolfberry | 0.1-5 |
| Sea Buckthorn | 3-10 |
| Water | 1-95 |
| Excipients** | 0.1-10 |

*Fruit extracts are selected from but not limited to Apple, Pear, Grape, Pinapple, and Cranberry

Examples IX

| Formulation | Composition (wt %) |
|---|---|
| Gac Fruit Puree | 4%-9% |
| Sea Buckthorn Juice | 4%-9% |
| Cili Juice | 1%-5% |
| Wolfberry Juice | <1% |
| Juice(s) from Concentrate* | 16%-27% |
| Excipients | <1% |

*Juices from concentrate can be selected from Grape, Pear, Apple, Cranberry, Carrot, Blueberry, and Tomato

Example X

The nutritional compositions of the present invention were tested and compared to conventional antioxidant containing nutritional supplements. Specifically, study groups were formed for each of the two antioxidant compositions. The study groups were generally comprised of healthy non-smokers between the ages of 18 and 65 years. The subjects were excluded from the studies if they had used antioxidant supplements within the prior three months. Subjects who were chosen to participate in the studies were instructed to complete a computer-administered questionnaire to assess demographical, dietary and lifestyle variables. Subjects then underwent carotenoid level testing in the skin on the palm of the hand using a BioPhotonic Scanner. On the same day as the initial baseline measurement, subjects were supplemented with either a conventional antioxidant containing nutritional supplement (Pharmanex LifePak® delivers 15 mg of carotenoids/day) or with a Gac Fruit containing antioxidant nutritional supplement of the present invention (Pharmanex G3™ delivers 9 mg of carotenoids/day). There were 28 participants who were supplemented the conventional antioxidant nutritional supplement and 10 participants who were supplemented with a Gac Fruit nutritional supplement. The skin carotenoid BioPhotonic response was measured at the 4 and 8 week time points. Statistical significance was examined in both studies.

Table 1 gives the test result measurements for the conventional antioxidant containing nutritional supplement group. Data points for some participants in the conventional supplement group were unable to be obtained.

TABLE 1

Conventional Antioxidant Containing Nutritional Supplement (Pharmanex LifePak ® - 15 mg carotenoids/day)

| | Week 0 (Baseline) | Week 4 | Week 8 | Change from Baseline - Week 4 | Change from Baseline - Week 8 |
|---|---|---|---|---|---|
| 1 | 19,700 | 26,400 | 29,300 | 6,700 | 9,600 |
| 2 | 18,500 | — | 24,600 | — | 6,100 |
| 3 | 12,100 | 19,200 | 24,000 | 7-100 | 11,900 |
| 4 | 21,200 | — | 20,600 | — | (600) |
| 5 | 31,500 | 38,100 | — | 6,600 | — |
| 6 | 15,000 | 21,100 | 24,600 | 6,100 | 9,600 |
| 7 | 27,400 | — | — | — | — |
| 8 | 19,600 | 27,500 | 33,400 | 7,900 | 13,800 |
| 9 | 24,900 | 32,300 | — | 7,400 | — |
| 10 | 22,000 | 26,400 | 34,600 | 4,400 | 12,000 |
| 11 | 10,700 | 13,300 | — | 2,600 | — |
| 12 | 19,100 | 24,600 | — | 5,500 | — |
| 13 | 28,100 | 33,800 | 31,700 | 5,700 | 3,600 |
| 14 | 14,500 | 19,200 | — | 4,700 | — |
| 15 | 13,100 | 18,700 | 19,400 | 5,600 | 6,300 |
| 16 | 17,300 | 21,400 | — | 4,100 | — |
| 17 | 16,100 | 25,700 | 26,600 | 9,600 | 10,500 |
| 18 | 14,700 | 29,300 | 33,900 | 14,600 | 19,200 |
| 19 | 20,300 | 30,300 | 34,700 | 10,000 | 14,400 |
| 20 | 16,400 | 21,700 | — | 5,300 | — |
| 21 | 28,700 | 40,900 | 46,400 | 12,200 | 17,700 |
| 22 | 14,700 | — | 16,300 | — | 1,600 |
| 23 | 19,900 | 27,300 | 33,000 | 7,400 | 13,100 |
| 24 | 15,100 | 28,000 | 33,700 | 12,900 | 18,600 |
| 25 | 32,300 | 42,600 | 44,700 | 10,300 | 12,400 |
| 26 | 17,000 | 24,600 | — | 7,600 | — |
| 27 | 28,200 | 30,200 | — | 2,000 | — |
| 28 | 20,500 | 22,000 | 24,900 | 1,500 | 4,400 |
| Mean | 19,950 | 26,858 | 29,800 | 6,992 | 10,267 |
| Std. Dev. | 5,951 | 7,141 | 8,047 | 3,315 | 5,744 |

Table 2 gives the test result measurements for the Gac Fruit containing nutritional supplement group.

TABLE 2

Gac Fruit Containing Antioxidant Nutritional Supplement
(Pharmanex G3 ™ - 9 mg carotenoids/day)

|   | Week 0 (Baseline) | Week 4 | Week 8 | Change from Baseline - Week 4 | Change from Baseline - Week 8 |
|---|---|---|---|---|---|
| 1 | 19,000 | 23,000 | 27,000 | 4,000 | 8,000 |
| 2 | 19,000 | 23,000 | 25,000 | 4,000 | 6,000 |
| 3 | 31,000 | 39,000 | 45,000 | 8,000 | 14,000 |
| 4 | 18,000 | 22,000 | 31,000 | 4,000 | 13,000 |
| 5 | 28,000 | 35,000 | 38,000 | 7,000 | 10,000 |
| 6 | 29,000 | 34,000 | 41,000 | 5,000 | 12,000 |
| 7 | 21,000 | 29,000 | 30,000 | 8,000 | 9,000 |
| 8 | 23,000 | 26,000 | 28,000 | 3,000 | 5,000 |
| 9 | 28,000 | 31,000 | 36,000 | 3,000 | 8,000 |
| 10 | 21,000 | 29,000 | 39,000 | 8,000 | 18,000 |
| Mean | 23,700 | 29,100 | 34,000 | 5,400 | 10,300 |
| Std. Dev. | 4,832 | 5,724 | 6,716 | 2,119 | 3,974 |

As can be seen from Tables 1 and 2, the Gac Fruit containing antioxidant composition provide a larger average increase of Raman intensity counts after eight weeks than the conventional supplement despite containing 40% less carotenoids per daily dose. Thus the carotenoids in the Gac Fruit containing composition are at least 40% bioavailable than those in the conventional nutritional supplement.

It is to be understood that the above-described arrangements are only illustrative of the application of the principles of the present invention. Numerous modifications and alternative arrangements may be devised by those skilled in the art without departing from the spirit and scope of the present invention. Thus, while the present invention has been fully described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of improving absorption of an antioxidant administered to a subject comprising co-administering at least one antioxidant, as part of a plant extract selected from the group consisting of Cili fruit extract, Siberian pineapple extract, Wolfberry extract, and mixtures thereof, with an effective amount of a Gac Fruit juice, wherein the antioxidant absorption is increase by at least about 15% as compared to an equivalent total antioxidant dosage that does not include a Gac Fruit juice.

2. The method of claim 1, wherein the antioxidant absorption is increased by at least about 25% as compared to an equivalent total antioxidant dosage that does not include a Gac Fruit juice.

3. The method of claim 1, wherein the antioxidant absorption is increased by at least about 40% as compared to an equivalent total antioxidant dosage that does not include a Gac Fruit juice.

4. The method of claim 1, wherein the Gac Fruit and the antioxidant are administered as a single nutritional composition.

5. The method of claim 4, wherein the Gac Fruit comprises from 0.1wt % to 20 wt % of the nutritional composition.

6. The method of claim 5, wherein the Gac Fruit comprises from 3.0wt % to about 15 wt % of the nutritional composition.

7. The method of claim 6, wherein the Gac Fruit comprises from 4.0wt % to about 9.0 wt % of the nutritional composition.

8. The method of claim 1, wherein the at least one plant extract comprises from about 0.1wt % to about 25 wt % of the nutritional composition.

9. The method of claim 1, wherein the at least one plant extract is a Cili fruit extract.

10. The method of claim 9, wherein the Cili fruit extract is present in an amount from about 0.5 wt % to about 10.0 wt % of the nutritional composition.

11. The method of claim 10, wherein the Cili fruit extract is present in an amount from about 1.0 wt % to about 5.0 wt % of the nutritional composition.

12. The method of claim 1, wherein the at least one plant extract is a Siberian pineapple extract.

13. The method of claim 12, wherein the Siberian pineapple extract is present in an amount from about 0.1 wt % to about 20.0 wt % of the nutritional composition.

14. The method of claim 12, wherein the Siberian pineapple extract is present in an amount from about 0.5 wt % to about 10.0 wt % of the nutritional composition.

15. The method of claim 12, wherein the Siberian pineapple extract is present in an amount from about 4 wt % to about 9.0 wt % of the nutritional composition.

16. The method of claim 1, wherein the at least one plant extract is a Wolfberry extract.

17. The method of claim 16, wherein the Wolfberry extract is present in an amount from about 0.01 wt % to about 10.0 wt % of the nutritional composition.

18. The method of claim 16, wherein the Wolfberry extract is present in an amount from about 0.1 wt % to about 5.0 wt % of the nutritional composition.

19. The method of claim 16, wherein the Wolfberry extract is present in an amount from about 0.2 wt % to about 1.0 wt % of the nutritional composition.

20. The method of claim 1, wherein the at least one plant extract is includes a Cili fruit extract and a Siberian pineapple extract.

21. The method of claim 20, wherein the Cili fruit extract is present in an amount of from about 0.01 wt % to about 10.0 wt % of the nutritional formulation and the Siberian pineapple extract is present in an amount of from about 0.1wt % to about 20.0 wt % of the nutritional composition.

22. The method of claim 1, wherein the at least one plant extract includes a Cili fruit extract and a Wolfberry extract.

23. The method of claim 22, wherein the Cili fruit extract is present in an amount of from 0.01 wt % to about 10.0 wt % of the nutritional formulation and the Wolfberry extract is present in an amount of from about 0.5 wt % to about 10.0 wt % of the nutritional composition.

24. The method of claim 1, wherein the at least one plant extract includes a Siberian pineapple Extract and Wolfberry extract.

25. The method of claim 24, wherein the Siberian pineapple extract is present in an amount of from about 0.1 wt % to about 20.0 wt % of the nutritional composition and the Wolfberry extract is present in an amount of from about 0.5 wt % to about 10.0 wt % of the nutritional composition.

26. The method of claim 1, wherein the at least one plant extract includes a Cili fruit extract, a Siberian pineapple extract, and a Wolfberry extract.

27. The method of claim 26, wherein the Cili fruit extract is present in an amount of from about 0.01 wt % to about 10.0 wt % of the nutritional formulation, the Siberian pineapple extract is present in an amount of from about 0.1 wt % to about 20.0 wt % of the nutritional composition, and the Wolfberry extract is present in an amount of from about 0.5 wt % to about 10.0 wt % of the nutritional composition.

28. The method of claim 7, wherein the nutritional composition includes excipients selected from the group consisting of flavorants, colorants, stabilizers, and preservatives.

* * * * *